United States Patent [19]
Nicholson

[11] Patent Number: 5,540,662
[45] Date of Patent: Jul. 30, 1996

[54] MEDICAL DEVICES

[75] Inventor: Peter J. Nicholson, Cricklade, England

[73] Assignee: The BOC Group plc, Windlesham, England

[21] Appl. No.: 354,173

[22] Filed: Dec. 12, 1994

[30] Foreign Application Priority Data

Dec. 10, 1993 [GB] United Kingdom .................. 9325350
Mar. 16, 1994 [GB] United Kingdom .................. 9405084

[51] Int. Cl.⁶ .................................................. A61M 5/00
[52] U.S. Cl. ........................... 604/110; 604/164; 604/198; 604/264
[58] Field of Search .................................. 604/164–165, 604/168–170, 158–159, 177, 192, 264, 272, 274, 198, 110; 606/185

[56] References Cited

U.S. PATENT DOCUMENTS

| | | |
|---|---|---|
| 4,820,267 | 4/1989 | Harman . |
| 5,098,392 | 3/1992 | Fleischhacker et al. . |
| 5,163,912 | 11/1992 | Gay et al. . |
| 5,186,712 | 2/1993 | Kelso et al. . |
| 5,215,528 | 6/1993 | Purdy et al. . |
| 5,232,450 | 8/1993 | Green et al. . |
| 5,312,345 | 5/1994 | Cole . |
| 5,317,345 | 5/1994 | Cole . |
| 5,342,382 | 8/1994 | Brinkerhoff et al. . |
| 5,364,365 | 11/1994 | Wortrich . |
| 5,388,589 | 2/1995 | Davis . |
| 5,431,676 | 7/1995 | Dubrul et al. . |

FOREIGN PATENT DOCUMENTS

| | | |
|---|---|---|
| 0546769A2 | 3/1992 | European Pat. Off. . |
| 89/92757 | 3/1989 | WIPO . |

*Primary Examiner*—Randall L. Green
*Assistant Examiner*—Perry E. Van Over
*Attorney, Agent, or Firm*—Roger M. Rathbun; Larry R. Cassett

[57] ABSTRACT

A medical device, for example, an IV cannula or a syringe which has a hollow needle 4 with a sharp distal end 6 for piercing the skin of a patient includes means for protecting the sharp end 6 of the needle 4 after use to minimise the possibility of accidental needle stick. The means includes a rod 12 mounted for movement through the needle 4 between a needle end protection position and a retracted position within the hollow needle 4; and means for maintaining the rod towards the needle end protection position.

10 Claims, 5 Drawing Sheets

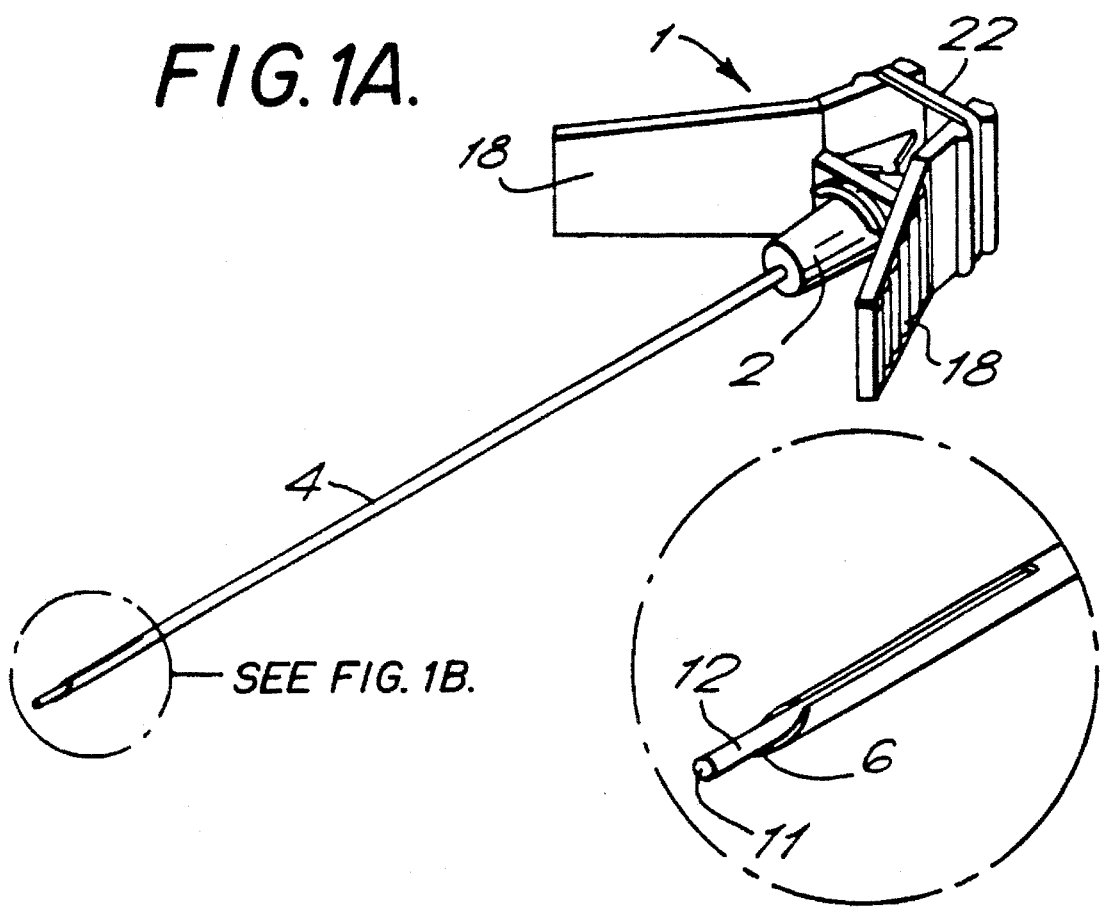
FIG. 1A.
FIG. 1B.
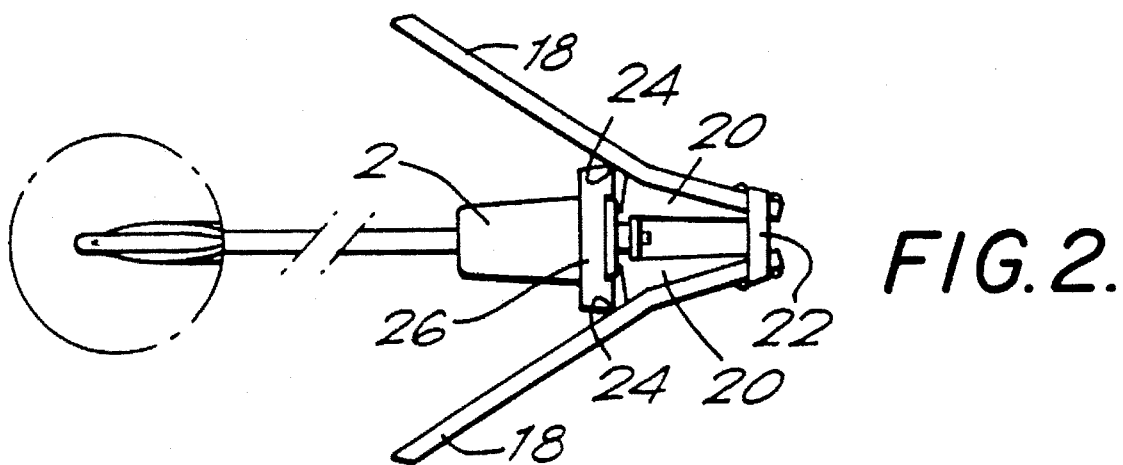
FIG. 2.

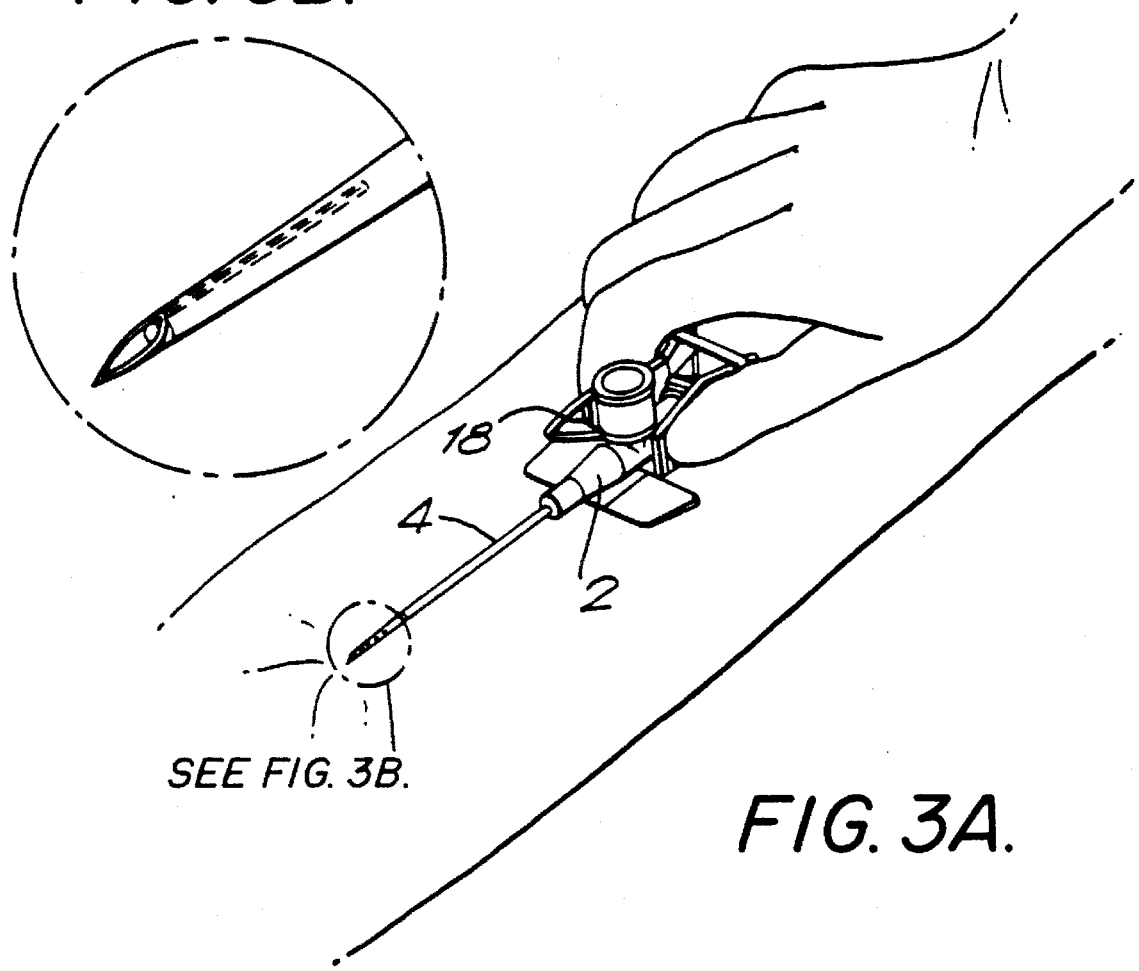
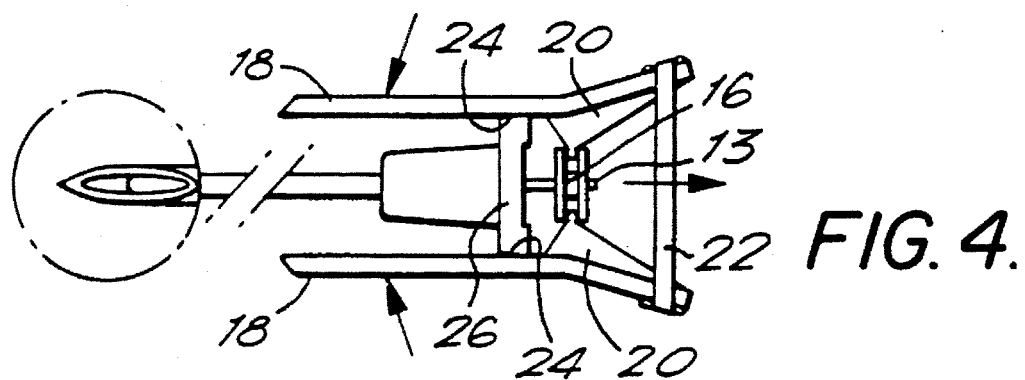

5,540,662

MEDICAL DEVICES

FIELD OF THE INVENTION

The present invention relates to medical devices and, in particular, to medical devices such as intravenous catheters and syringes which include a hollow needle having a sharp distal end for piercing the skin of a patient.

The existence of infectious diseases such as AIDS and hepatitis has highlighted the danger to which medical personnel may be exposed when treating patients by means of catheter devices and syringes where a sharp needle point is used to pierce the skin of the patient. Medical personnel have been infected by physical contact with or an accidental prick by an infected needle (needle stick).

In order to protect medical personnel against inadvertent needle stick, a number of solutions have been developed whereby protective means incorporated within a catheter or syringe prevents physical contact with the needle after use and hence against inadvertent needle stick.

Many of the developments are complicated and involve the retraction of the needle within a housing once the needle has been used. These complications add to the expense as well as the manufacturing difficulties involved in providing adequate anti-needle stick protection.

It is an aim of the present invention to provide a simple but effective means for protecting the point of a needle forming part of a medical device such as a catheter or syringe in order to minimise the possibility of inadvertent needle stick.

According to the present invention, a medical device comprises a hollow needle having a sharpened distal end for piercing the skin of a patient and includes means for protecting said sharpened distal end after use to minimize the possibility of inadvertent needle stick, said means comprising a rod mounted for reciprocal movement through the hollow needle between a first needle end protection position at which an end of the rod is level with or extends beyond the sharpened distal end of the needle, and a second retracted position in which said end is positioned within the hollow needle and spaced from said sharpened distal end, and means maintaining the rod towards the first needle end protection position.

Preferably, the rod is solid although it could be hollow with a blunt distal end.

In one embodiment the needle extends from the distal end of a grip, the rod extending through the needle and the grip such that its proximal end extends beyond the grip, and means attached at or adjacent the proximal end of the rod is engageable by co-operating means for reciprocating the rod through said needle and grip.

The means attached at or adjacent the proximal end of the rod is preferably a bobbin which is engaged by two wing members, each wing member being mounted on an individual side arm, the side arms being located one on each side of the grip, the arrangement being such that when the side arms are pressed together the wing members will cause the bobbin and hence the rod to move from the first to the second position.

The maintaining means may be an elastic member extending between the side arm.

In an alternative embodiment the needle extends from the distal end of a housing and the maintaining means includes a shoulder formed in the rod which in the second position of the rod engages behind a resilient collar forming part of the housing thereby preventing movement of the rod from the second towards the first position.

Preferably the rod is undercut to form the shoulder which engages behind the resilient collar located at the proximal end of the housing.

The maintaining means may include a resilient shoulder formed on an interior surface of the housing.

BRIEF DESCRIPTION OF THE DRAWINGS

Embodiments of the invention will now be described, by way of example, reference being made to the Figures of the accompanying diagrammatic drawings in which:

FIG. 1A is a perspective view of an IV cannula;

FIG. 1B is an enlarged perspective view of a portion of the IV cannula of FIG. 1A;

FIG. 2 is a plan view of the IV cannula of FIG. 1;

FIG. 3A is a perspective view of the IV cannula of FIG. 1A illustrating a cannula needle about to be inserted into the skin of a patient and including a coupling and a pair of fixation wings not illustrated in FIG. 1A;

FIG. 3B is an enlarged perspective view of a portion of the IV cannula of FIG. 1A;

FIG. 4 is a plan view illustrating the position of side arm of the cannula at the moment of insertion of the needle into the skin of a patient;

DESCRIPTION OF THE PREFERRED EMBODIMENT

Figure 5:
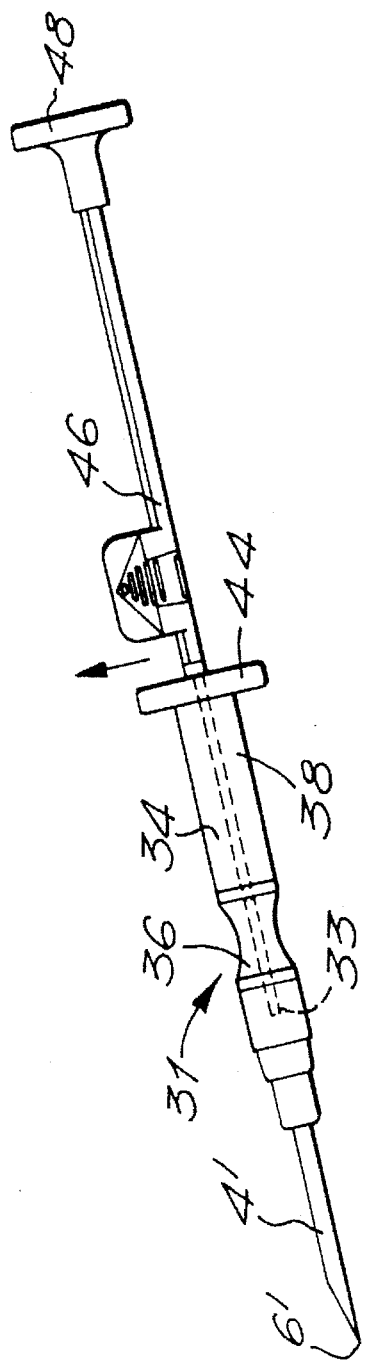
FIG. 5 is a side view of a medical syringe for piercing the skin of a patient to deliver a drug.

Referring first to the embodiment of the invention as illustrated in FIGS. 1A to 4, as shown, an IV cannula 1 includes a grip 2 from which extends a hollow needle 4 having a sharpened distal end 6.

Extending through the grip 2 and the needle 4 is a solid rod 12. The rod 12 has a distal end 11 and, as shown most clearly in FIG. 4, a proximal or rear end 13. Affixed at or adjacent the proximal end 13 of the rod 12 is a bobbin 16. A pair of side arms 18 is located one on each side of the grip 2 and each carries a wing member 20 engaging the bobbin 16. Connecting the rear ends of the side arms 18 is an elastic member 22.

As shown, the inside surface 24 of each side arm 18 bears against an enlarged flange portion 26 of the grip 2 such that without any pressure being applied to the side arms 18 said side arms 18 will naturally adopt the position illustrated in FIGS. 1A and 2 by virtue of the force applied by the elastic member 22 to the rear ends of the side arms 18.

Before use, the cannula 1 will be as illustrated in FIGS. 1A and 2 with the rear ends of the side arms 18 pulled closely together and the bobbin 16 positioned flush against the rear end of the grip 2.

However, when it is required that the sharpened distal end 6 of the needle 4 pierce the skin of a patient then the side arms 18 are first pressed or squeezed together as illustrated in FIG. 3 against the bias of the elastic member 22. Squeezing or pressing the side arms 18 together to the position illustrated in FIG. 4 will cause the wing members 20 to move the bobbin 16 and hence the rod 12 rearwardly so that the distal end 11 of the rod 12 is retracted into the hollow needle 4 and is thereby spaced from said sharpened end 6 of the needle 4. This will allow the sharpened end 6 of the needle 4 to be used to pierce the skin of a patient.

Once the needle 4 is removed from the body of the patient and the squeezing force removed from the side arms 18 then the elastic member 22 will again apply a force to the side arms 18 bringing them back to the position shown in FIGS. 1 and 2. This will have the effect of the wing members 18 engaging the bobbin 16 to move the bobbin 16 and hence the rod 12 forwardly through the hollow needle 4 until the distal end 11 of the rod 12 again extends level with or beyond the sharpened distal end 6 of the needle.

A particular advantage of the embodiment described above is the simplicity of the means for protecting the sharpened distal end 6 of the needle 4 which avoids the use of complicated and expensive solutions to the anti-needle stick problem.

Referring now to the embodiment of the invention as illustrated in FIG. 5 to 9, as shown, a syringe 31 for implanting a drug beneath the skin of a patient comprises a hollow needle 4' having a sharp distal end $6^z$ extending from the distal end of a housing 34. The housing 34 comprises two parts 36, 38 integrally joined together. As shown parts 36, 38 have aligned passages 40, 42. A drug 33 or other substance to be administered to a patient is initially located in the passage 40 of part 36.

The part 38 includes a collar 44 at its proximal end made of resilient material.

In the ready-to-use condition a rod 12' extends outwardly from the proximal end of the part 38. The rod 12' at its proximal end is provided with a button 48. Adjacent the button 48 the surface of the rod is undercut to form a rearwardly facing annular shoulder 50.

Prior to its use, the syringe 31 is provided with a detachable spacer 46 which engages around the rod 12' between the collar 44 and the button 48 to prevent accidental movement of the rod inwardly through the housing 34. In this position the distal end of the rod 12' is located in the passage 42 of the part 38 and as previously explained the drug 33 is located in passage 40 of the part 36.

Figure 6:
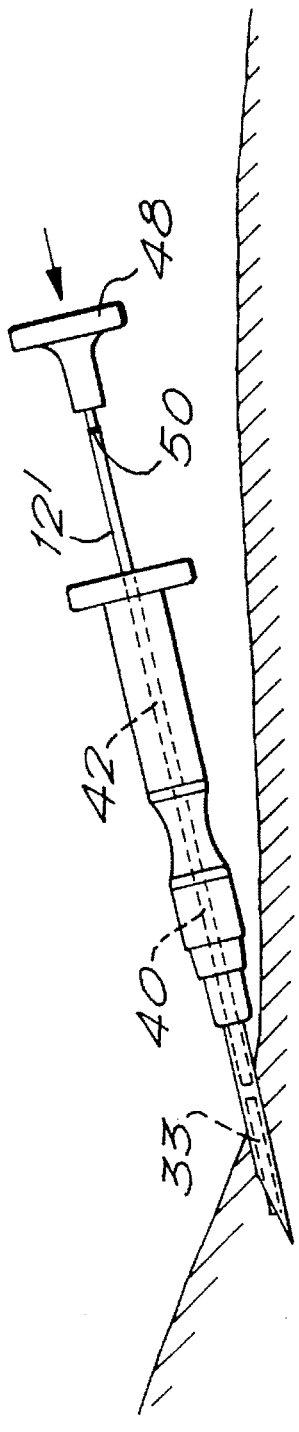
FIG. 6 is a view of the syringe similar to FIG. 5 but showing the syringe piercing the skin of the patient.

In use, when it is desired to place the drug 33 beneath the skin of a patient, the spacer 46 is removed and the sharp end 6' of the needle 4' is caused to pierce the skin of the patient as shown in FIG. 6.

Next pressure is applied to the button 48 causing the rod $12^z$ to pass through the passages 40, 42 and engage the drug 33.

Figure 7:
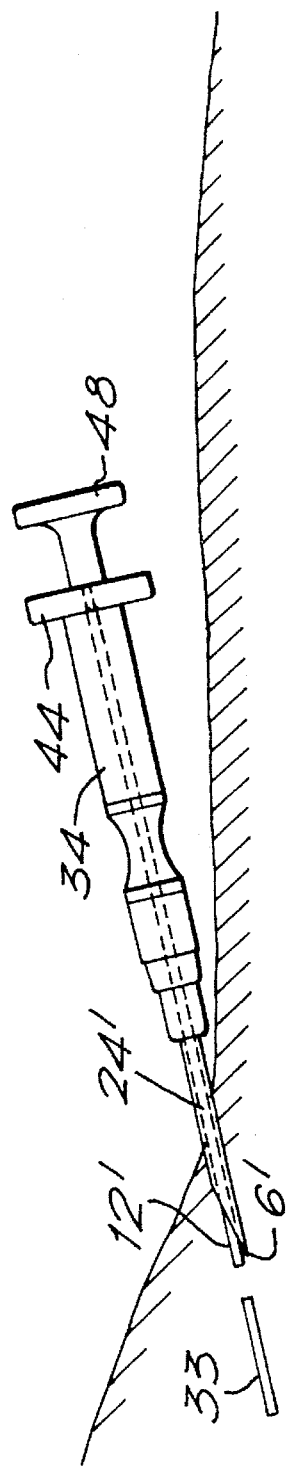
FIG. 7 is a view similar to the views of FIGS. 5 and 6 but showing the drug now delivered subcutaneously.

Further movement of the rod 12' through the passage 40 and the hollow needle 4' causes the drug 33 to pass along and out from the hollow needle 4 (FIG. 7).

Figure 8:
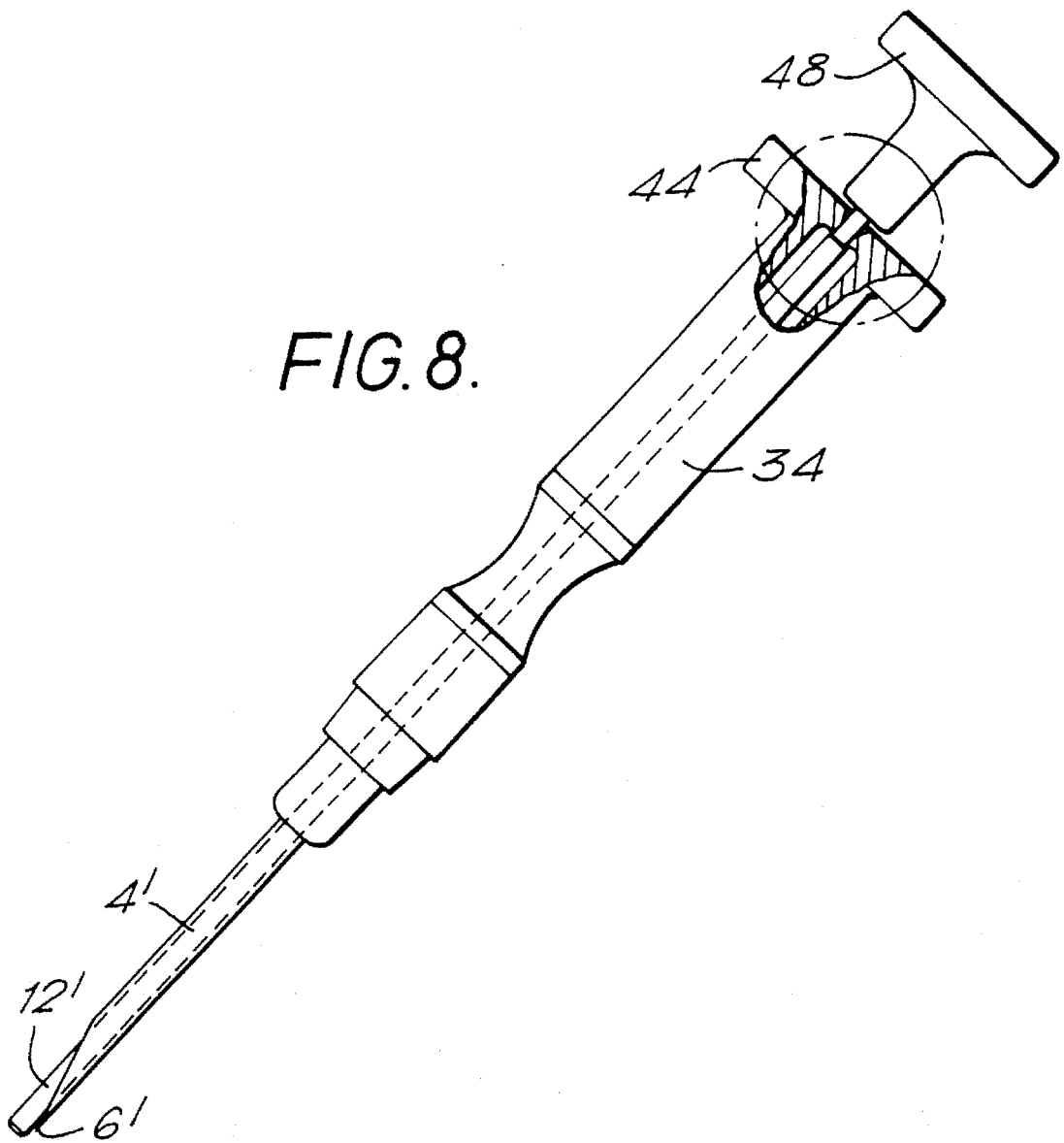
FIG. 8 is a view similar to FIG. 7 with the needle tip of the syringe protected and with a part sectioned to illustrate a locking feature.
Figure 9:
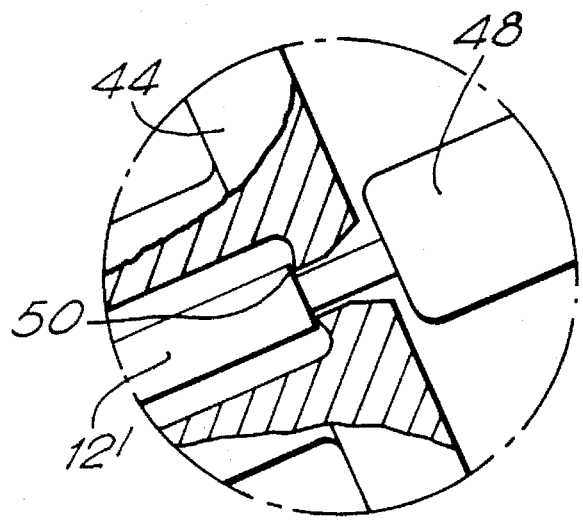
FIG. 9 is an enlarged detail of the sectioned part of FIG. 8.

In its final position the distal end of the rod 12' extends beyond the sharp end 6' of the needle 4' and the shoulder 50 engages against the inner surface of the resilient collar 44 (FIGS. 8 and 9).

Thus, when the needle 4' is withdrawn from the skin of the patient its sharp end $6^z$ is protected by the rod 12' thereby preventing accidental needle stick and enabling safe disposal of the syringe. Further, by virtue of the shoulder 50 engaging the inside surface of the resilient collar 44, the rod 12' is located in its needle end protection position and cannot be withdrawn from the needle to expose the sharp end 6'.

Referring now to FIGS. 10 to 13, an over-needle introducer 51 for positioning a catheter into the vein of a patient comprises a hollow needle 52 having a sharp distal end 53 extending from the distal end of a housing 54. As shown, the needle 52 is anchored at its proximal end within the housing 54. Located rearwardly of the proximal end of the needle 52 within the housing 54 for movement along the interior of the housing 54 is an assembly 55 comprising a rod 56, a central star-shaped member 57 and extending rearwardly therefrom an elongate striker 59. The central star-shaped member 57 is provided with serrations for aspiration and blood flash back in a manner known in the art.

The interior surface of the housing 54 adjacent its proximal end is tapered to converge towards a portion 61 with substantially parallel sides. A shoulder 63 is formed in the interior surface which separates portion 61 from an adjacent portion 65.

Figure 10:
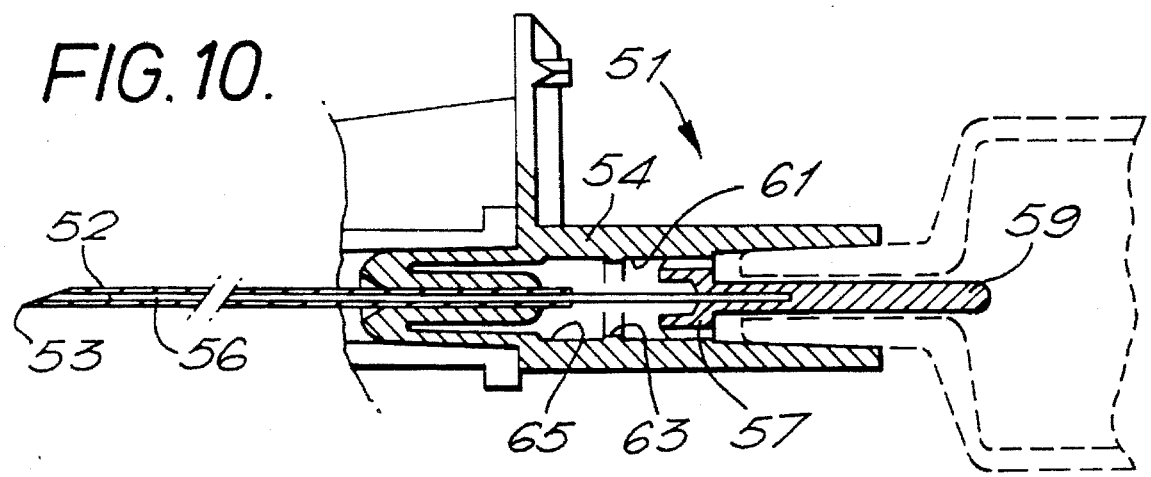
FIG. 10 is a side view in cross-section of an over-needle introducer.
Figure 11:
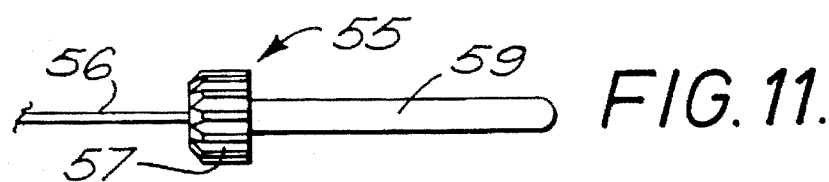
FIG. 11 is a side view of an anti-needle stick rod forming part of the introducer of FIG. 10.

In use a catheter (not shown) extends over the needle 52, the skin of a patient is pierced by the sharp end 53 of the needle 52 such that the catheter is positioned in a blood vessel of the patient and the needle 52 is withdrawn leaving the catheter in place in the blood vessel, for example, a vein, in a manner known in the art. During this operation, the assembly 55 is located in the interior of the housing 54 such that the member 57 is positioned in the portion 61 with the striker 59 extending out from the rear or proximal end of the housing 54 and the rod 56 extends through a portion of the hollow needle 52 but with a gap between the sharp end 53 of the needle 52 and the distal end of the rod 56 as shown in FIG. 10.

Figure 12:
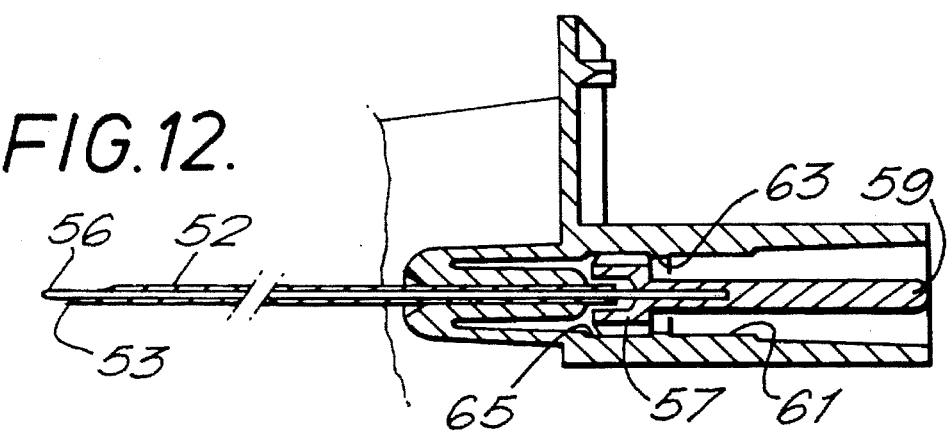
FIG. 12 is a side view in cross-section similar to FIG. 10 but showing the anti-needle stick rod in a second needle protection position.
Figure 13:
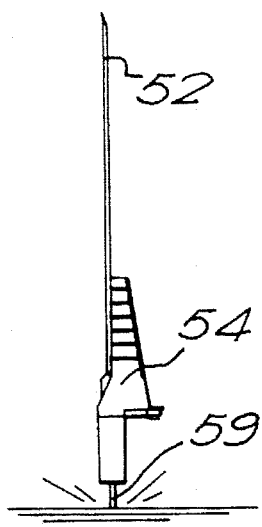
FIG. 13 is a view illustrating a method of moving the anti-needle stick rod from the position illustrated in FIG. 10 to the second needle protection position illustrated in FIG. 12.

Once the needle 52 is withdrawn from the patient, the end of the striker 59 extending from the rear end of the housing 54 is struck or is caused to strike a surface (see FIG. 13) such that the member 57 is forced from the portion 61 over the resilient shoulder 63 into the portion 65 such that the distal end of the rod 56 extends well beyond the sharp end 53 of the needle 52 as illustrated in FIG. 12.

Thus, the sharp end 53 of the needle 52 is guarded against accidental needle stick thereby preventing the used needle 52 from inadvertently piercing the skin of the user.

The rod 56 is locked against movement back through the hollow needle 52 by the shoulder 63 engaging with the rear-facing surface of the member 57.

A particular advantage of the embodiments described above is the simplicity of the means for locking the rod 12, 12' in its needle protecting position which avoids the use of complicated and expensive solutions to the anti-needle stick problem.

Although reference has been made in the above described embodiments to an IV cannula, a syringe and an over-needle introducer the anti-needle stick concept can be applied to other medical devices which involve the use of a hollow needle.

I claim:

1. A medical device comprising a hollow needle having a sharpened distal end for piercing the skin of a patient and including means for protecting said sharpened distal end after removal of said hollow needle from the patient to minimize the possibility of inadvertent needle stick, said means comprising a rod mounted to said hollow needle for captive reciprocal movement through said hollow needle between a first needle end protection position at which an end of the rod is level with or extends beyond the sharpened distal end of said hollow needle and a second retracted position in which said end is positioned within said hollow needle and spaced from said sharpened distal end and means for maintaining the rod towards the first needle end protection position.

2. A medical device as claimed in claim 1, in which the rod is solid.

3. A medical device as claimed in claim 1, in which the needle extends from the distal end of a grip, the rod extending through the needle and the grip such that its proximal end extends beyond the grip, and means attached at or adjacent the proximal end of the rod engageable by co-operating means for reciprocating the rod through said needle and grip.

4. A medical device as claimed in claim 3, in which the means attached at or adjacent the proximal end of the rod is a bobbin which is engaged by two wing members, each wing member being mounted on an individual side arm, the side arms being located one on each side of the grip, the arrangement being such that when the side arms are pressed together the wing members will cause the bobbin and hence the rod to move from the first to the second position.

5. A medical device as claimed in claim 4, in which the maintaining means is an elastic member extending between the side arms.

6. A medical device as claimed in claim 1, in which the medical device is an intravenous catheter.

7. A medical device as claimed in claim 1, in which the needle extends from the distal end of a housing and the maintaining means includes a shoulder formed in the rod which in the second position of the rod engages behind a resilient collar forming part of the housing hereby preventing movement of the rod from the second towards the first position.

8. A medical device as claimed in claim 7, in which the rod is undercut to form the shoulder which engages behind the resilient collar located at the proximal end of the housing.

9. A medical device as claimed in claim 1, in which the maintaining means includes a resilient shoulder formed on an interior surface of the housing.

10. A medical device as claimed in claim 9, in which the rod is connected to a striker which in the first position of the rod extends outwardly from the proximal end of the housing.

* * * * *